US011992057B2

(12) United States Patent
Tan et al.

(10) Patent No.: US 11,992,057 B2
(45) Date of Patent: May 28, 2024

(54) ATOMIZER PROVIDING REDUCED NUMBER OF ASSEMBLY TIMES AND PREVENTING OIL LEAKAGE AND POLLUTION OF ATOMIZED LIQUID

(71) Applicant: SHENZHEN BOSHANG TECHNOLOGY CO., LTD, Shenzhen (CN)

(72) Inventors: Guangqian Tan, Shenzhen (CN); Pengjiang Zhai, Shenzhen (CN)

(73) Assignee: SHENZHEN BOSHANG TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/095,611

(22) Filed: Jan. 11, 2023

(65) Prior Publication Data
US 2023/0165311 A1 Jun. 1, 2023

Related U.S. Application Data

(63) Continuation of application No. PCT/CN2021/091714, filed on Apr. 30, 2021.

(30) Foreign Application Priority Data

Aug. 31, 2020 (CN) .......................... 202021872272.8
Nov. 18, 2020 (CN) .......................... 202022680374.6
(Continued)

(51) Int. Cl.
*A24F 40/48* (2020.01)
*A24F 40/10* (2020.01)
(Continued)

(52) U.S. Cl.
CPC .............. *A24F 40/48* (2020.01); *A24F 40/10* (2020.01); *A24F 40/42* (2020.01); *A24F 40/46* (2020.01)

(58) Field of Classification Search
CPC .......... A24F 40/10; A24F 40/42; A24F 40/46; A24F 40/40; A24F 40/48
See application file for complete search history.

(56) References Cited

U.S. PATENT DOCUMENTS 9,955,734 B2 * 5/2018 Lin .......................... A24F 40/70
10,196,188 B2 * 2/2019 Liu .......................... A24F 40/42
(Continued)

FOREIGN PATENT DOCUMENTS

| CN | 203776165 U | 8/2014 |
| CN | 203952433 U | 11/2014 |

(Continued)

*Primary Examiner* — Hae Moon Hyeon
(74) *Attorney, Agent, or Firm* — Jeenam Park (57) ABSTRACT

The present disclosure provides an atomizer providing reduced number of assembly times and preventing oil leakage and pollution of atomized liquid. The atomizer includes: a central rod, a first sleeve, a suction nozzle and a first seal; the first sleeve is sleeved on the central rod, and an annular gap formed between the first sleeve and the central rod forms an oil storage bin; the suction nozzle is set on the top of the center rod and blocks the top of the first sleeve; the suction nozzle and the center rod are integrally formed; the suction nozzle is arranged with an oil filling port; the first seal is arranged between the first sleeve and the central rod, and is used for blocking the oil filing port.

15 Claims, 7 Drawing Sheets

(30) Foreign Application Priority Data

| Nov. 18, 2020 | (CN) | .......................... 202022682057.8 |
| Nov. 18, 2020 | (CN) | .......................... 202022683386.4 |
| Nov. 18, 2020 | (CN) | .......................... 202022683387.9 |

(51) Int. Cl.
*A24F 40/42* (2020.01)
*A24F 40/46* (2020.01)

(56) References Cited

U.S. PATENT DOCUMENTS

| 10,306,929 | B2 * | 6/2019 | Liu | ...................... A61M 11/042 |
| 10,986,868 | B2 * | 4/2021 | Chen | ........................ H05B 3/34 |
| 11,083,224 | B2 * | 8/2021 | Lin | .......................... A24F 40/48 |
| 2016/0015082 | A1 * | 1/2016 | Liu | .......................... A24F 40/44 |
| | | | | 131/329 |
| 2016/0286860 | A1 * | 10/2016 | Flayler | ................. A61M 11/042 |

FOREIGN PATENT DOCUMENTS

| CN | 204232291 | U | | 4/2015 |
| CN | 105054300 | A | | 11/2015 |
| CN | 105919163 | A | | 9/2016 |
| CN | 207011691 | U | | 2/2018 |
| CN | 207040900 | U | | 2/2018 |
| CN | 305512246 | S | | 12/2019 |
| CN | 210248385 | U | | 4/2020 |
| CN | 111329128 | A | | 6/2020 |
| CN | 211091895 | U | | 7/2020 |
| CN | 217471240 | U | * | 9/2022 |
| EP | 3037008 | A1 | | 6/2016 |

\* cited by examiner

# ATOMIZER PROVIDING REDUCED NUMBER OF ASSEMBLY TIMES AND PREVENTING OIL LEAKAGE AND POLLUTION OF ATOMIZED LIQUID

CROSS-REFERENCE TO RELATED APPLICATIONS

The present application is a 35 U.S.C. § 371 National Phase conversion of International Application No. PCT/CN20211091714 filed Apr. 30, 2021, which claims foreign priority of Chinese Patent Application No. 202021872272.8, filed on Aug. 31, 2020, Chinese Patent Application No, 202022683387.9, filed on Nov. 18, 2020, Chinese Patent Application No. 202022683386.4, filed on Nov. 18, 2020, Chinese Patent Application No. 202022680374.6, filed on Nov. 18, 2020, and Chinese Patent Application No. 202022682057.8, filed on Nov. 18, 2020, in the State Intellectual Property Office of China, the contents of all of which are hereby incorporated by reference.

TECHNICAL FIELD

The present disclosure relates to a new type of atomizer, which belongs to the technical field of atomization devices.

BACKGROUND

Atomization inhalation therapy is to disperse the drug into tiny mist or particles with an atomization device, suspend it in the gas, and enter the respiratory tract and lungs to the goal of clean the airway, humidify the airway, local treatment and systemic treatment. Atomization inhalation is currently the most effective way for respiratory therapy and lung care.

An electronic atomizer is a device that atomizes the atomized liquid by means of high temperature, high pressure or ultrasound. When the existing electronic atomizer is filled with oil, the suction nozzle is usually disassembled for oil filling, and then the suction nozzle is covered after the oil filling is completed. Since the suction nozzle and the central rod are separate parts, this leads to, dust and sundries can easily enter the atomizer and pollute the atomizing liquid. At the same time, the suction nozzle and the central rod need to be disassembled and assembled many times during oil filling, and multiple assemblies will cause risks to the oil seal of the atomizer, and it is easy to cause oil leakage phenomenon, thus affecting the normal use of the atomizer.

SUMMARY

The present disclosure provides a new type of atomizer which can solve the problems that the structure of the existing atomizer needs to be assembled many times, and oil leakage and atomized liquid pollution are easy to occur.

The present disclosure provides a new type of atomizer, including: an atomizer body and an atomizer base, the atomizer base is arranged at the bottom end of the atomizer body for fixing the atomizer body;

the atomizer body includes a central rod, a first sleeve, a suction nozzle and a first seal;
the first sleeve is sleeved on the central rod, and a gap formed between the first sleeve and the central rod constitutes an oil storage bin;
the suction nozzle is arranged on the top of the central rod and blocks the top of the first sleeve; the suction nozzle is integrally formed with the central rod; the suction nozzle is arranged with an oil filling port; the oil filling port connected with the oil storage bin;
the first seal is arranged between the first sleeve and the central rod, and is used to block the oil filling port.

Optional, the first seal is arranged at an end of the central rod which close to the suction nozzle;
the first seal is sleeved on the central rod, and clamped with the central rod.

Optional, the central rod is arranged with a slot; the first seal is snapped into the slot.

Optional, there are two oil filing ports; the two oil filing ports are symmetrically distributed about the central axis of the suction nozzle.

Optional, the inner side wall of the atomizer base is riveted to the outer side wall of the bottom end of the central rod.

Optional, the material of the central od is ceramic; the shape of the bottom end of the central rod is oval.

Optional, the material of the atomizer base is metal.

Optional, the riveting depth between the inner side wall of the atomizer base and the outer side wall of the bottom end of the central rod is 3 mm to 8 mm.

Optional, a second seal is also arranged between the central rod and the first sleeve, and the second seal is sleeved on the outer side wall of the central rod; the second seal and the outer side wall of the central rod is snapped.

Optional, a second sleeve is sleeved on the outer side wall of the atomizer base; the second sleeve is engaged with the outer side wall of the atomizer base; the material of the second sleeve is a heat insulating material.

Optional, the second sleeve is a plastic part.

Optional, the outer side wall of the atomizer base is arranged with grooves; the inner side wall of the second sleeve is arranged with protrusions at corresponding positions; and the protrusions can be clipped into the grooves.

Optional, there are multiple grooves and protrusions; the multiple grooves are evenly distributed around the outer side wall of the atomizer base.

Optional, the ends close to each other of the second sleeve and the first sleeve abut against each other; the inner side wall of the second sleeve is riveted to the outer side wall of the atomizer base.

Optional, the novel atomizer also includes a heating element assembly;
the heating element assembly is located at the bottom end of the central rod, and an atomizing channel is arranged on the side wall of the central rod, and the atomizing channel is used to transport a smoke oil in the oil storage bin to the heating element body; the heating element assembly is used to atomizer the smoke oil;
one end of the top surface of the second seal close to the central rod is flush with the bottom end of the channel opening of the atomizing channel, and the height of the end of the top surface of the second seal far away from the central rod is between the bottom end of the channel opening and the top end of the channel opening of the atomizing channel.

Optional, the top surface of the second seal is a stepped surface or an inclined surface.

Optional, the outer side walls of the first seal and the second seal are engaged with the inner side wall of the first sleeve.

Optional, both the first seal and the second seal are silicone sealing rings.

Optional, the material of the first sleeve is glass.

The beneficial effects of the present disclosure include:

(1) The new type of atomizer provided by the present disclosure can reduce the number of assembly times and ensure the consistency of the assembly process by setting the suction nozzle and the central rod to be integrally formed, so that the assembly is simple and oil leakage is not easy to occur. After the parts of the atomizer are assembled into finished products, oil is added to prevent dust and debris from falling into the atomizer, thereby avoiding contamination of the atomized liquid.

(2) In the new type of atomizer provided by the present disclosure, the inner side wall of the atomizer base is riveted to the outer side wall of the bottom end of the central rod, so that the connection between the atomizer base and the central rod is stable; at the same time, adjusting the riveting depth between the central rod and the base of the atomizer by the connection method, the problem of insufficient size of the central rod can be compensated.

(3) The new type of atomizer provided by the present disclosure is arranged with a heat-insulating second sleeve on the outer side wall of the atomizer base; using the second sleeve to replace the steel ring in the prior art can effectively weaken the heat generated during the suction process of the atomizer base, greatly reduces the phenomenon of hot hands when touching; at the same time, the present disclosure sets the second sleeve to engage with the outer side wall of the atomizer base, which can effectively prevent the second sleeve from falling off, thereby improving the user experience.

(4) In the new type of atomizer provided by the present disclosure, the suction nozzle and the central rod is integrally formed, and then setting the first sleeve outside the central rod, using the suction nozzle to limit the top position of the first sleeve, and using the second sleeve set the atomizer base to defines the bottom position of the first sleeve, so that the position of the first sleeve is fixed, then there is no need to use glue to fix it with the central rod, thus avoiding the use of glue, reducing the number of assembly times, and saving user costs and improve user experience.

(5) In the new type of atomizer provided by the present disclosure, a second seal is arranged between the first sleeve and the central rod, and the end of the top surface of the second seal close to the central rod and the channel opening bottom of the atomization channel are arranged. The height of the end of the top surface of the second seal away from the central rod is between the bottom end of the channel opening of the atomization channel and the top end of the channel opening; in this way, by increasing the height of the second seal, the liquid level of the smoke oil in the oil storage bin can be raised, so that the smoke oil can effectively flow from the atomization channel to the heating element assembly inside the central rod for atomization, Since the end of the top surface of the second seal away from the central rod is higher than the end of the top surface of the second seal near the central rod, it further promotes the flow of smoke oil into the central rod, and solves the problem that the atomizer is not clean, and saves user costs.

LIST OF PARTS AND REFERENCE NUMBERS

10. Atomizer body; 11. Central rod; 12. First sleeve; 13. Suction nozzle; 14. First seal; 15. Oil filling port; 16. Atomizer base; 17. Second seal; 18. Second sleeve; 19. Oil storage bin; 20. Slot; 21. Groove; 22. Protrusion; 23. Atomizing channel; 24. Heating element assembly; 1102. Outer side wall of the bottom end of the central rod; 1103. Outer side wall of the central rod; 1201. Inner side wall of the first sleeve; 1402. Outer side wall of the first seal; 1601. Inner side wall of the atomizer base; 1602. Outer side wall of the atomizer base; 1702. Outer side wall of the second seal; 1703. Top surface of the second seal; 1802. Inner side wall of the second sleeve.

DETAILED DESCRIPTION

The present disclosure is described in detail below in conjunction with the examples, but the present disclosure is not limited to these examples.

In the description of the present disclosure, it should also be noted that, unless otherwise clearly specified and limited, the terms "arrange", "installation" and "connection" should be understood in a broad sense, for example, it may be a fixed connection, it can also be a detachable connection or an integral connection; it can be a mechanical connection or an electrical connection; it can be a direct connection or an indirect connection through an intermediary, and it can be the internal communication of two components. Those of ordinary skill in the art can understand the specific meanings of the above terms in the present disclosure in specific situations.

Figure 1:
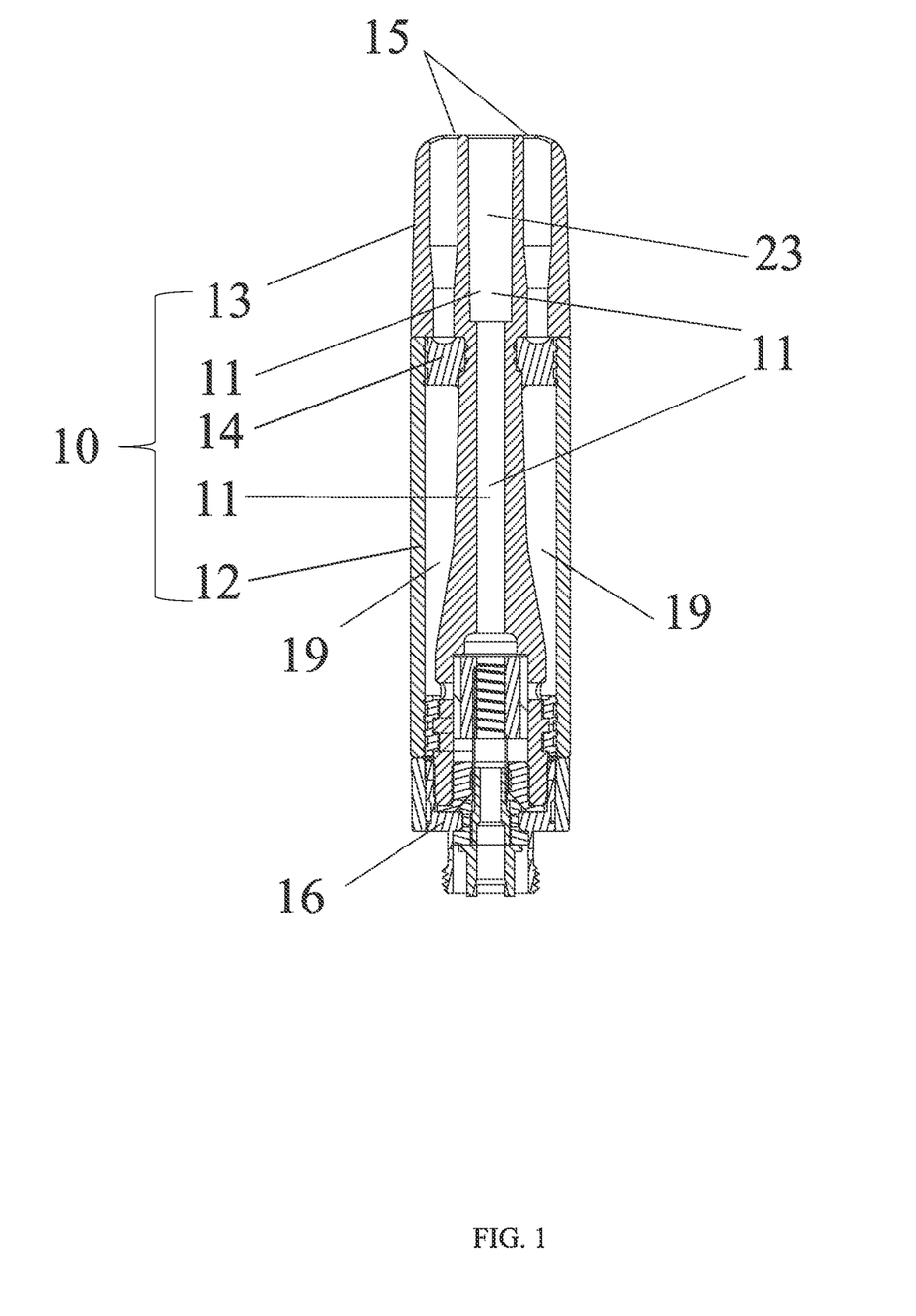
FIG. 1 is a first schematic diagram of an atomizer according to an embodiment of the present disclosure.
Figure 2:
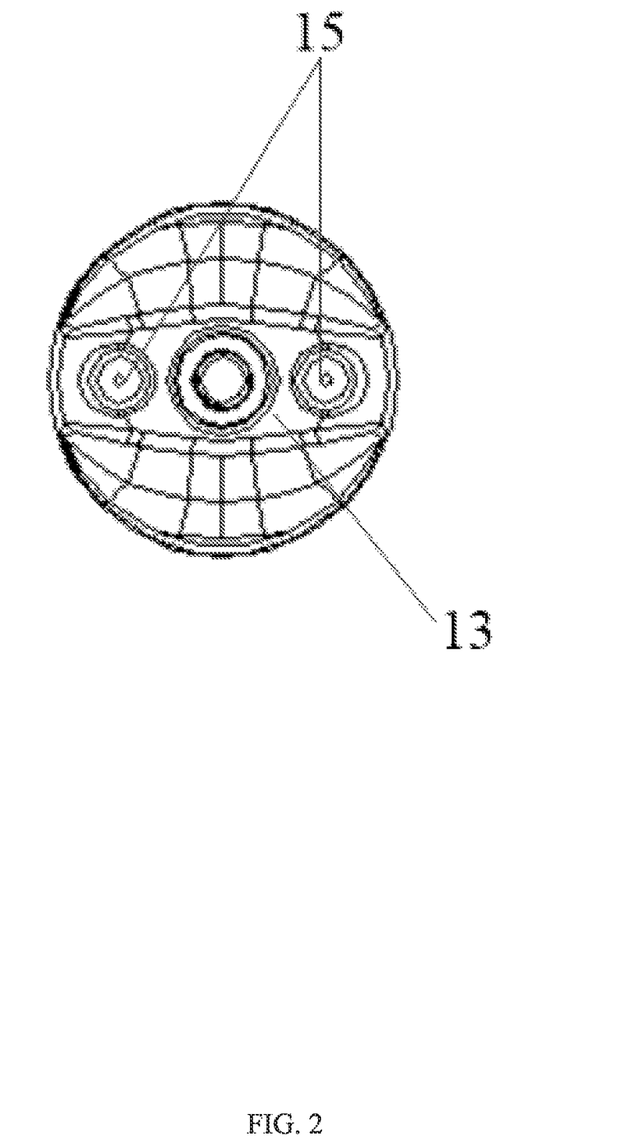
FIG. 2 is a top view of structure diagram of an of atomizer according to an embodiment of the present disclosure.

The embodiment of the present disclosure provides a new type of atomizer, as shown in FIG. 1 and FIG. 2, including: an atomizer body and an atomizer base, the atomizer base is arranged at the bottom end of the atomizer body for fixing the atomizer base to the atomizer body 10; the atomizer body 10 includes a central rod 11, a first sleeve 12, a suction nozzle 13 and a first seal 14; the first sleeve 12 is sleeved on the central rod 11, and a gap formed between the first sleeve 12 and the central rod 11 constitutes an oil storage bin 19, the oil storage bin 19 is used to hold the smoke oil; the suction nozzle 13 is arranged on the top of the central rod 11 and blocks the top of the first sleeve 12; the suction nozzle 13 is integrally formed with the central rod 11; the suction nozzle 13 is arranged with an oil filling port 15; the oil filling port 15 connected with the oil storage bin 19; the first seal 14 is arranged between the first sleeve 12 and the central rod 11, and is used to block the oil filling port 15.

In the embodiment of the present disclosure, the central rod 11 is in the shape of a hollow straw, and the first sleeve 12 is in the shape of an elongated cylindrical sleeve.

Referring to FIG. 1 and FIG. 2, since the suction nozzle 13 is integrally formed with the central rod 11, an oil filling port 15 needs to be arranged on the suction nozzle 13, and the oil filling port 15 connected with the oil storage bin 19, so that the smoke oil can be supplied to the oil storage bin 19 through the oil filling port 15. In order to prevent the smoke oil in the oil storage bin 19 from leaking from the oil filling port 15, a first seal 14 can be set between the first sleeve 12 and the central rod 11, and the first seal 14 can block the oil filling port 15; in a specific oiling operation, an oiling needle can penetrate the first seal 14 and extend into the oil storage bin 19 for oiling. When the oiling is completed, the first seal 14 can automatically recover to play a role of sealing and blocking the oil filling port 15.

In this disclosure, by setting the suction nozzle 13 and the central rod 11 to be integrally formed, the number of assembly can be reduced, the consistency of the assembly process can be ensured, the assembly is simple, and oil leakage is not easy to occur; in addition, the present disclosure can add oil after the entire atomizer parts are assembled into a finished product, to prevent dust and debris from falling into the atomizer, thereby avoiding contamination of the atomized liquid.

In practical applications, the first seal 14 can be set to be sleeved on the central rod 11 and be engaged with the central rod 11. Specifically, the first seal 14 is arranged at an end of the central rod 11 close to the suction nozzle 13. A slot 20 is arranged on the central rod 11; the first seal 14 is snapped into the slot 20. This can prevent the first seal 14 from falling off, so that it can play a sealing effect after filling with oil. In order to further prevent the first seal 14 from falling, an outer side wall 1402 of the first seal 14 may be configured to engage with an inner side wall 1201 of the first sleeve 12.

The embodiment of the present disclosure does not limit the material of the first seal 14. In practical applications, the first seal 14 can be selected to be a silicone part, for example, a silicone sealing ring can be selected.

The embodiment of the present disclosure does not limit the number, shape and size of the oil filling ports 15. In order to facilitate quick oil filling, two oil filling ports 15 can generally be arranged on the suction nozzle 13. The two oil filling ports 15 are distributed symmetrically about the central axis of the suction nozzle 13. The oil filling port 15 can be set as a circular port.

In order to facilitate the user to observe the remaining amount of smoke oil in the oil storage bin 19, this implementation can optionally use a transparent or translucent first sleeve 12, for example, a glass first sleeve 12, the glass first sleeve 12 does not only have good transparency, but also have stable chemical properties and will not chemically react with the smoke oil in the oil storage bin 19, ensuring that users can enjoy the taste of the mist.

Existing electronic atomizers are usually small in size for portability, so the size of their internal structural parts is also small. In order to facilitate the connection between structural parts, most of them are fixed by glue bonding in the industry. For example, the inner side wall 1601 of the atomizer base 16 is bonded to the outer side wall 1102 of the bottom end of the central rod 11 to complete the connection between the atomizer base 16 and the central rod 11. However, when glue is used for bonding, the glue is difficult to control evenly, so it is easy to cause sticking. The connection effect is not good, and the connection between the structural parts is not firm.

Figure 3:
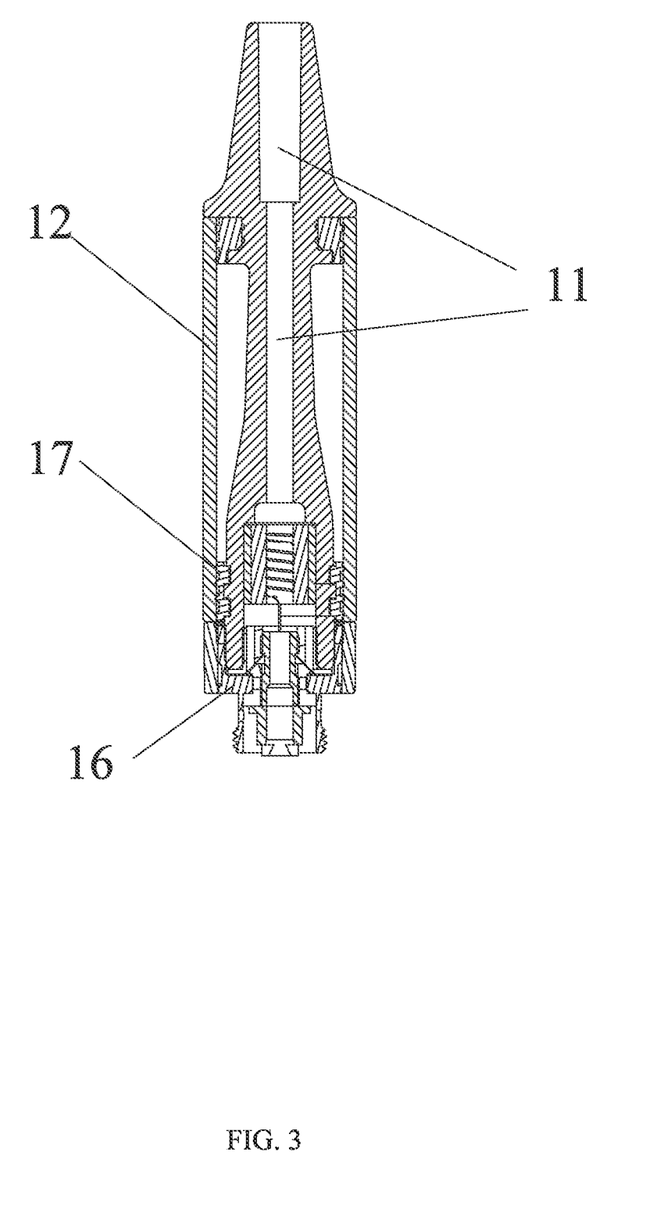
FIG. 3 is a second schematic diagram of an atomizer according to an embodiment of the present disclosure.

In order to overcome this problem, as shown in FIG. 3, in the present disclosure, the inner side wall 1601 of the atomizer base 16 is riveted to the outer side wall 1102 of the bottom end of the central rod 11. This makes the connection between the atomizer base 16 and the central rod 11 stable; at the same time, this connection can compensate for the insufficient size of the central rod 11 by adjusting the riveting depth of the central rod 11 and the atomizer base 16.

Since ceramics are clean and beautiful, the material of the central rod 11 can be selected as ceramics. However, ceramics are fragile, so if the ceramic inner riveting method is used, that is, the outer side wall 1102 of the bottom end of the ceramic central rod 11 is connected with the inner side wall 1601 of the atomizer base 16 by riveting, it is easy to cause the cracking of the ceramic central rod 11; therefore, in the present disclosure, the inner side wall 1601 of the atomizer base 16 is connected by riveting to the outer side wall 1102 of the bottom end of the central rod 11. By adopting this ceramic outer riveting method, the cracking of the ceramic central rod 11 can be well avoided.

During actual manufacture, the shape of the bottom end of the central rod 11 can be processed into an oval shape.

The embodiment of the present disclosure does not limit the material of the atomizer base 16, in order to connect with the central rod 11 by riveting, the material of the atomizer base 16 is generally metal. In practical applications, the material of the atomizer base 16 can be selected as copper.

The embodiment of the present disclosure does not limit the specific riveting depth of the inner side wall 1601 of the atomizer base 16 and the outer side wall 1102 of the bottom end of the central rod 11, and those skilled in the art can set it according to the actual situation. In practical applications, the riveting depth of the inner side wall 1601 of the atomizer base 16 and the outer side wall 1102 of the bottom end of the central rod 11 can be selected to be 3 mm to 8 mm. Preferably, the riveting depth between the inner side wall 1601 of the atomizer base 16 and the outer side wall 1102 of the bottom end of the central rod 11 is 5 mm.

Referring to FIG. 3, a second seal 17 is also arranged between the central rod 11 and the first sleeve 12, and the second seal 17 is sleeved on the outer side wall 1103 of the central rod 11; the second seal 17 and the outer side wall 1103 of the central rod 11 is clipped. By providing the second seal 17, the atomized liquid in the atomizer body can be well prevented from leaking out.

The embodiment of the present disclosure does not limit the material of the second seal 17. In practical applications, the second seal 17 can be selected as a silicone sealing ring.

Existing electronic atomizers often use a steel ring as a decoration at the atomizer base 16, or use ceramics as a whole as a shell, which makes the position of the steel ring very hot during the suction process, thereby affecting the user experience; at the same time, in the prior art, the steel ring is usually riveted on the atomizer base 16, but this connection method has poor connection stability, which makes the steel ring easy to fall off from the atomizer base, thereby making the user experience poor.

Figure 4:
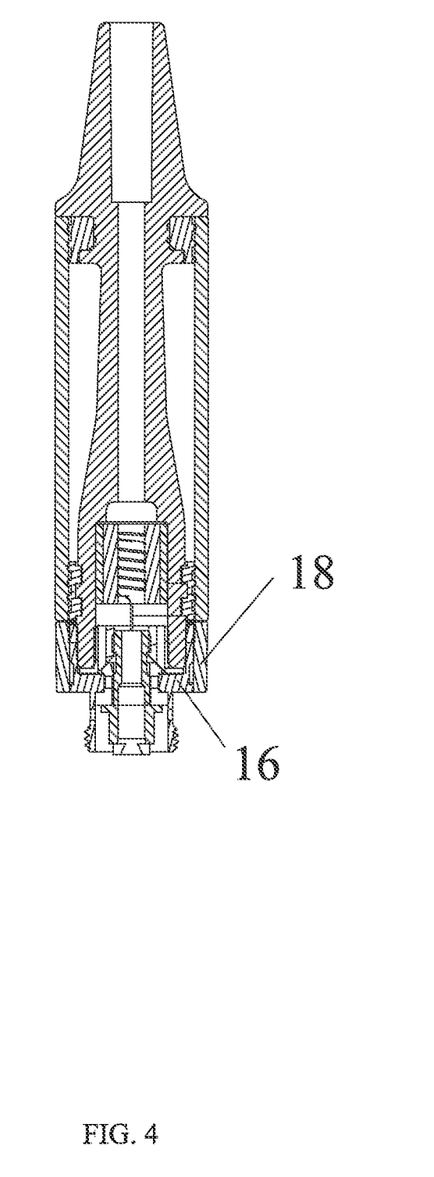
FIG. 4 is a third schematic diagram of an atomizer according to an embodiment of the present disclosure.

In order to overcome the above problems, as shown in FIG. 4, the present disclosure sets a second sleeve 18 on the outer side wall 1602 of the atomizer base 16; the second sleeve 18 is engaged with the outer side wall 1602 of the atomizer base 16; the material of the second sleeve 18 is a heat insulating material. In the present disclosure, the second sleeve 18 is sheathed on the outer side wall 1602 of the atomizer base 16; the second sleeve 18 is used to replace the steel ring in the prior art, which can effectively weaken the suction of the atomizer base 16. The heat generated during the process greatly reduces the phenomenon of hot hands when touched; at the same time, the present disclosure sets the second sleeve 18 to engage with the outer side wall 1602 of the atomizer base 16, which can effectively prevent the second sleeve 18 from falling off, thereby improving the user experience.

The embodiment of the present disclosure does not limit the material of the second sleeve 18, and in a practical application, the second sleeve 18 can be made of plastic parts or rubber rings.

The embodiment of the present disclosure does not limit the specific structure of the engagement between the second sleeve 18 and the outer side wall 1602 of the atomizer base 16, as long as the second sleeve 18 can be fixed and the purpose of preventing the second sleeve 18 from being pulled out can be achieved. For example, grooves 21 are provided on the outer side wall 1602 of the atomizer base 16; protrusions 22 are arranged at corresponding positions on the inner side wall 1802 of the second sleeve 18; the protrusions 22 can be engaged in the grooves 21. In order to achieve a better clamping effect between the second sleeve 18 and the outer side wall 1602 of the atomizer base 16, multiple grooves 21 and protrusions 22 can be arranged; the plurality of grooves 21 are evenly distributed around the outer side wall 1602 of the atomizer base 16. Further, there are three grooves 21 and three protrusions 22.

In the existing electronic atomizer, the suction nozzle assembly and the atomizing assembly are usually two separate parts, and the central rod 11 and the sleeve sleeved on it in the atomizing assembly are generally fixed with UV (ultraviolet) glue. After being fixed with glue, air bubbles will appear at the glue position and the glue will turn yellow, which will affect the user experience.

Figure 5:
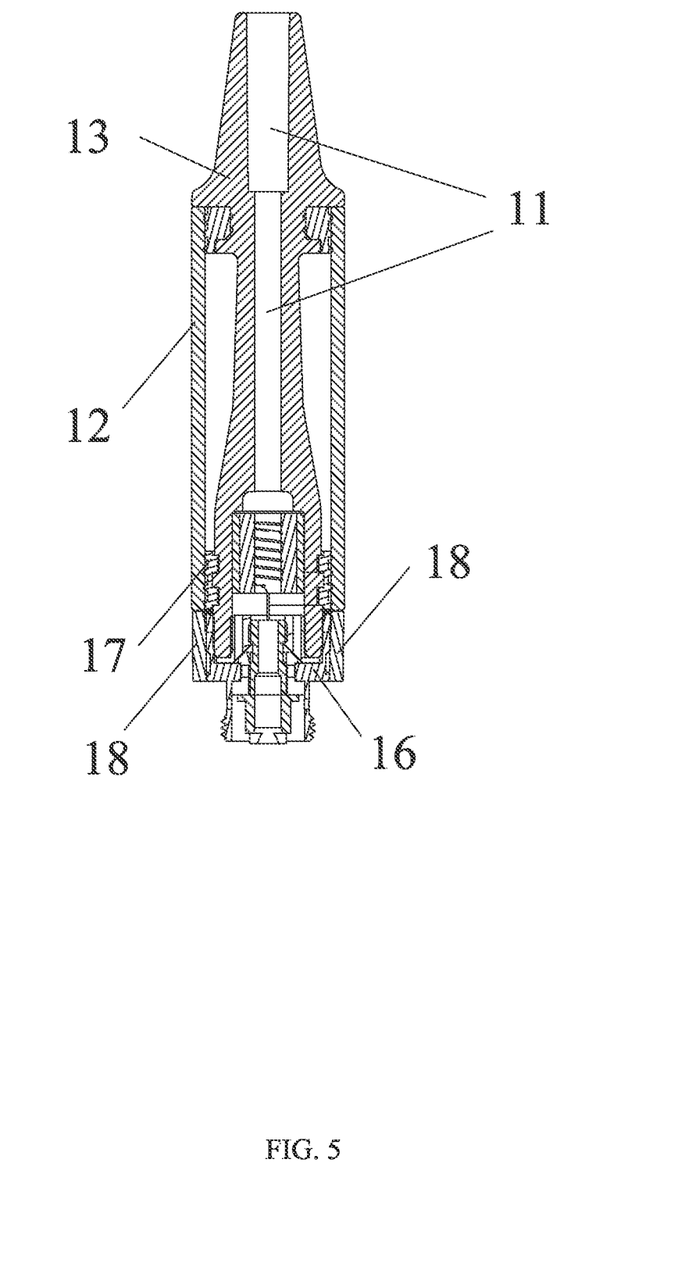
FIG. 5 is a forth schematic diagram of an atomizer according to an embodiment of the present disclosure.
Figure 6:
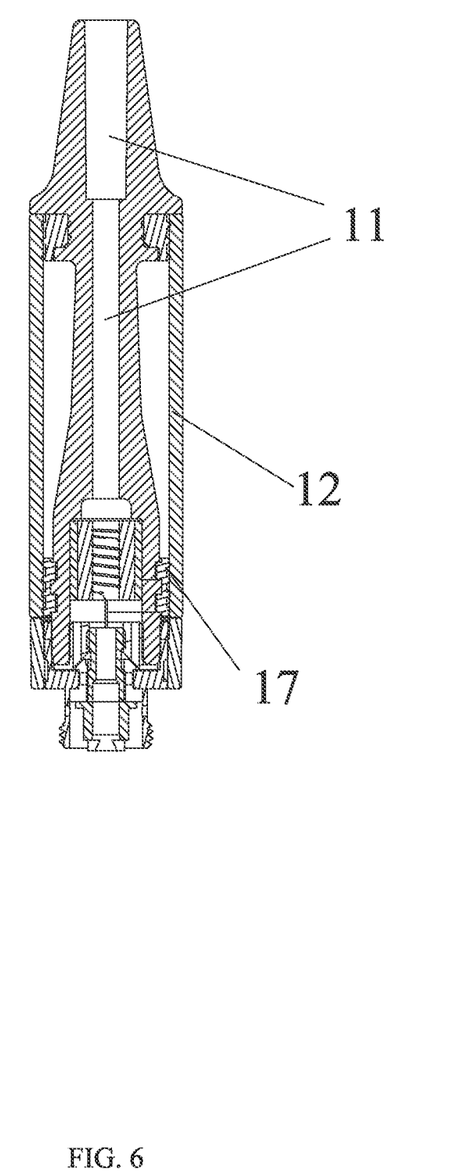
FIG. 6 is a fifth schematic diagram of an atomizer according to an embodiment of the present disclosure.
Figure 7:
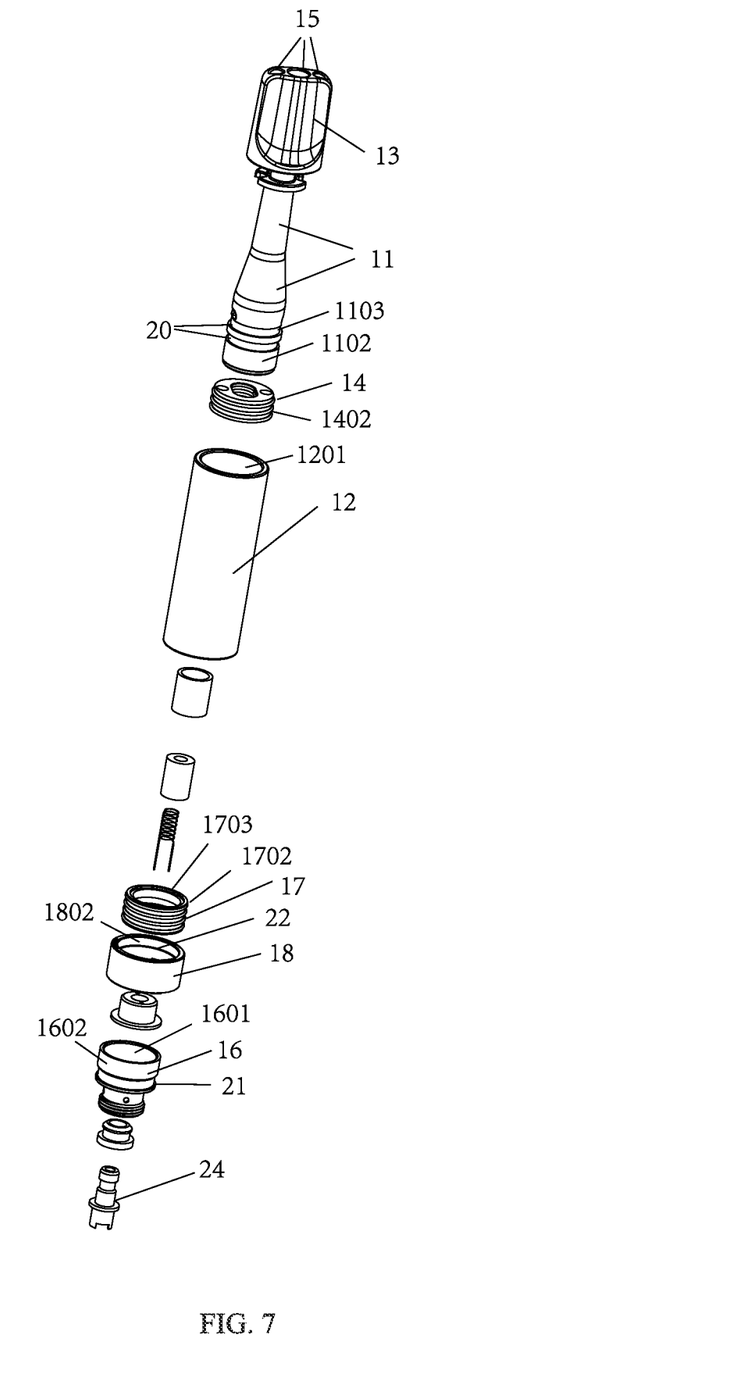
FIG. 7 is an exploded view of an atomizer according to an embodiment of the present disclosure.

In order to overcome the above problems, as shown in FIG. 5, the present disclosure sets the second sleeve 18 abutting against the end portions of the first sleeve 12; In the present disclosure, since the suction nozzle 13 and the central rod 11 are integrally formed, and then the first sleeve 12 is placed outside the central rod 11, the top position of the first sleeve 12 is defined by the suction nozzle 13, and the second sleeve 18 sleeved with the atomizer base 16 defines the bottom end position of the first sleeve 12, so that the position of the first sleeve 12 is fixed, so that there is no need to use glue to fix it with the central rod 11, thus avoiding the use of glue and reducing the number of assembly times saves user costs and improves user experience. At the same time, the inner side wall 1802 of the second sleeve 18 is riveted to the outer side wall 1602 of the atomizer base 16, which can well fix the second sleeve 18 and limit the position of the first sleeve 12 at the same time.

Existing electronic atomizers have the problem of unclean oil extraction during use, which leads to higher user costs. In order to overcome this problem, the novel atomizer provided by the present disclosure also includes a heating element assembly 24; the smoke oil in the oil storage bin 19 is delivered to the heating element assembly 24; the heating element assembly 24 is used to atomizer the smoke oil; the end of the top surface of the second seal 17 close to the central rod 11 is flush with the bottom end of the opening of the atomizing channel 23. The height of the end of the top surface of the second seal 17 away from the central rod 11 is located between the bottom end of the channel opening and the top end of the channel opening of the atomizing channel 23.

In this way, by raising the second seal 17, the liquid level of the smoke oil in the oil storage bin 19 can be raised, so that the smoke oil can effectively flow from the atomizing channel 23 to the heating element assembly 24 inside the central rod 11 for atomizing. Since the end of the top surface of the second seal 17 away from the central rod 11 is higher than the end of the top surface of the second seal 17 close to the central rod 11, it further promotes the flow of smoke oil into the central rod 11 and solves the problem of atomization. The problem of unclean oil pumping is solved, which saves the user's cost.

In the embodiment of the present disclosure, the end of the top surface of the second seal 17 away from the central rod 11 is higher than the end of the top surface of the second seal 17 close to the central rod 11, and there are various structures that can be realized, the top surface of the second seal 17 is a stepped surface; or the top surface of the second seal 17 is an inclined surface; this is not limited in this embodiment of the present disclosure.

In practical applications, the second seal 17 can be set to be sleeved on the central rod 11 and snapped to the central rod 11, Specifically, a slot 20 is provided on the central rod 11; the second seal 17 is snapped into the slot 20. This prevents the second seal 17 from falling off. In order to further prevent the second seal 17 from falling off, the outer side wall 1702 of the second seal 17 can be set to engage with the inner side wall 1201 of the first sleeve 12.

The above are only a few embodiments of the present disclosure, and do not limit the present disclosure in any form. Although the present disclosure is disclosed as above with preferred embodiments, it is not intended to limit the disclosure. Any skilled person familiar with this field, without departing from the scope of the technical solution of this disclosure, making some changes or modifications using the technical content disclosed above are equivalent to equivalent implementation cases, and all belong to the scope of the technical solution.

What is claimed is:

1. An atomizer, comprising: an atomizer body and an atomizer base,
   the atomizer base is arranged at the bottom end of the atomizer body for fixing the atomizer base to the atomizer body;
   the atomizer body comprises a central rod, a first sleeve, a suction nozzle, and a first seal;
   the first sleeve is sleeved on the central rod, and a gap formed between the first sleeve and the central rod constitutes an oil storage bin;
   the suction nozzle is arranged on the top of the central rod and blocks the top of the first sleeve; the suction nozzle is integrally formed with the central rod; the suction nozzle is arranged with an oil filling port; wherein the oil filling port is connected with the oil storage bin;
   the first seal is arranged between the first sleeve and the central rod, and is used to block the oil filling port;
   wherein the first seal is arranged at an end of the central rod which close to the suction nozzle;
   the first seal is sleeved on the central rod, and clamped with the central rod;
   wherein the central rod is arranged with a slot; the first seal is snapped into the slot;
   wherein an inner side wall of the atomizer base is connected to an outer side wall of the bottom end of the central rod.

2. The atomizer according to claim 1, wherein there are two oil filing ports; wherein, the two oil filing ports are symmetrically distributed about the central axis of the suction nozzle.

3. The atomizer according to claim 1, wherein the material of the central rod is ceramic; the shape of the bottom end of the central rod is oval.

4. The atomizer according to claim 1, wherein the material of the atomizer base is metal.

5. The atomizer according to claim 4, wherein a riveting depth between the inner side watt of the atomizer base and the outer side wall of the bottom end of the central rod is 3 mm to 8 mm.

6. The atomizer according to claim 1, wherein a second seal is arranged between the central rod and the first sleeve, and the second seal is sleeved on the outer side wall of the bottom end of the central rod; the second seal and an outer side wall of the central rod is snapped.

7. The-atomizer according to claim 6, wherein the atomizer further comprises a heating element assembly;
the heating element assembly is located at the bottom end of the central rod, and an atomizing channel is arranged on a side wall of the central rod, and the atomizing channel is used to transport a smoke oil in the oil storage bin to the heating element assembly; the heating element assembly is used to atomizer the smoke oil;
one end of the top surface of the second seal close to the central rod is flush with bottom end of a channel opening of the atomizing channel, and the height of the end of the top surface of the second seal far away from the central rod is between the bottom end of the channel opening and the top end of the channel opening of the atomizing channel.

8. The atomizer according to claim 7, wherein the outer side walls of the first seal and the second seal are engaged with the inner side wall of the first sleeve.

9. The atomizer according to claim 7, wherein both the first seal and the second seal are silicone sealing rings.

10. The atomizer according to claim 1, wherein a second sleeve is sleeved on an outer side wall of the atomizer base; the second sleeve is engaged with the outer side wall of the atomizer base; the material of the second sleeve is a heat insulating material.

11. The atomizer according to claim 10, wherein the second sleeve is a plastic part.

12. The atomizer according to claim 10, wherein the outer side wall of the atomizer base is arranged with a groove; an inner side wall of the second sleeve is arranged with a protrusion at a corresponding position; and the protrusions is clipped into the groove.

13. The atomizer according to claim 10, wherein the ends close to each other of the second sleeve and the first sleeve abut against each other; an inner side wall of the second sleeve is connected to the outer side wall of the atomizer base.

14. The atomizer according to claim 1, wherein the material of the first sleeve is glass.

15. The atomizer according to claim 1, wherein a second seal is also arranged between the central rod and the first sleeve, and the second seal is sleeved on the outer wall of the bottom end of the central rod; the second seal and the outer wall of the central rod is snapped.

* * * * *